(12) United States Patent
Zandifar et al.

(10) Patent No.: US 8,090,184 B2
(45) Date of Patent: Jan. 3, 2012

(54) FAULT DETECTION OF A PRINTED DOT-PATTERN BITMAP

(75) Inventors: Ali Zandifar, Cupertino, CA (US); Kar-Han Tan, Santa Clara, CA (US)

(73) Assignee: Seiko Epson Corporation, Tokyo (JP)

( * ) Notice: Subject to any disclaimer, the term of this patent is extended or adjusted under 35 U.S.C. 154(b) by 789 days.

(21) Appl. No.: 12/178,123

(22) Filed: Jul. 23, 2008

(65) Prior Publication Data

US 2010/0021048 A1 Jan. 28, 2010

(51) Int. Cl.
*G06K 9/00* (2006.01)
(52) U.S. Cl. .................................................. 382/141
(58) Field of Classification Search .................. None
See application file for complete search history.

(56) References Cited

U.S. PATENT DOCUMENTS

| | | |
|---|---|---|
| 4,185,298 A | 1/1980 | Billet et al. |
| 4,578,810 A | 3/1986 | MacFarlane et al. |
| 5,517,235 A | 5/1996 | Wasserman |
| 6,219,442 B1 | 4/2001 | Harper et al. |
| 6,434,264 B1 | 8/2002 | Asar |
| 6,477,266 B1 | 11/2002 | Asar |
| 6,546,528 B1 | 4/2003 | Sasaki et al. |
| 6,591,021 B1 * | 7/2003 | Breiter et al. .................. 382/274 |
| 6,641,983 B1 | 11/2003 | Lee et al. |
| 6,681,038 B2 | 1/2004 | Vilella |
| 6,724,473 B2 | 4/2004 | Leong et al. |
| 6,795,186 B2 | 9/2004 | Aspir et al. |
| 6,856,707 B2 * | 2/2005 | Enomoto ....................... 382/277 |
| 6,862,373 B2 * | 3/2005 | Enomoto ....................... 382/263 |
| 6,969,864 B2 | 11/2005 | Ye et al. |
| 6,970,588 B1 | 11/2005 | Komatsu |
| 7,027,639 B2 | 4/2006 | Fishbaine |
| 7,167,583 B1 | 1/2007 | Lipson et al. |
| 2003/0080727 A1 | 5/2003 | Yamauchi et al. |
| 2007/0146695 A1 | 6/2007 | Brouwer et al. |

* cited by examiner

*Primary Examiner* — Tu Nguyen

(57) ABSTRACT

Embodiments of the present invention enable fault detection in a printed dot-pattern image. Certain applications of the present invention are its use in various embodiments of a system for inspection of a printed circuit board ("PCB") substrate. In embodiments, a generated distortion map is based on a comparison of a reconstructed dot-pattern image, a simulated reference bitmap, and an error map representing differences between the reconstructed dot-pattern image and the reference bitmap. In embodiments, the pixels of the distortion map are color coded to identify the locations and types of aberrations that were discovered as a result of the comparison.

14 Claims, 9 Drawing Sheets

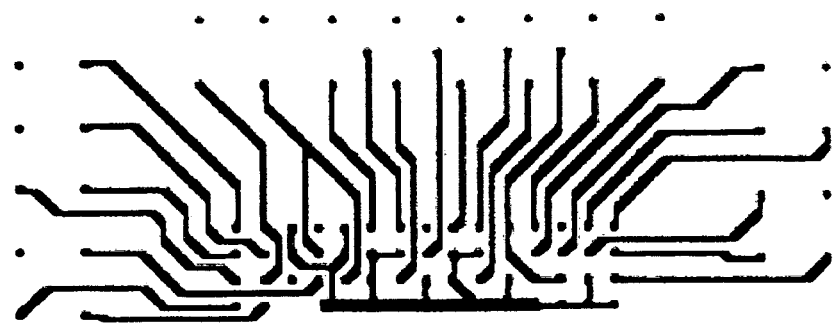
reference bitmap
120
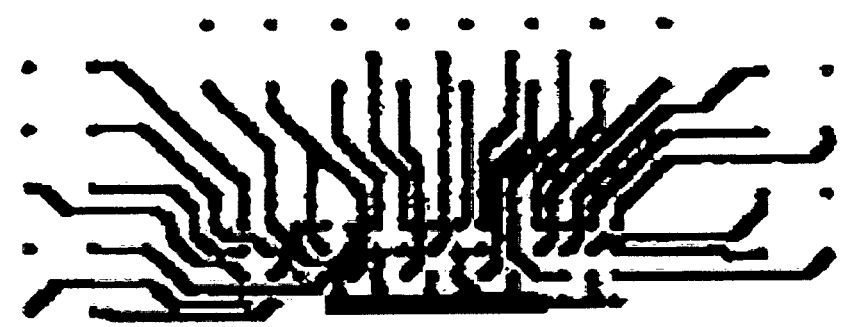
input image
140
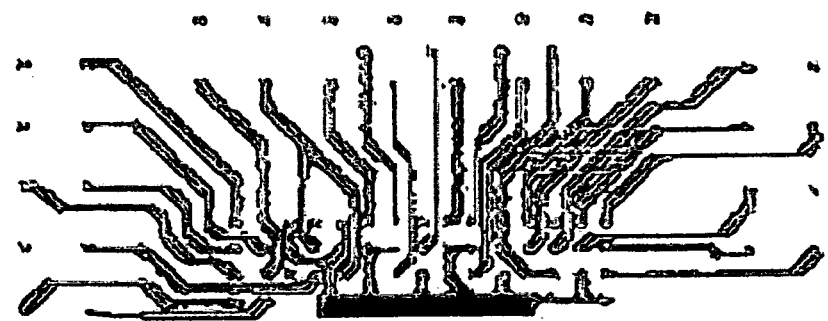
distortion map
160
FIGURE 1

600

```
┌─────────────────────────────────────┐
│ Compute the minimum acceptable error width │
│ and height in pixels based on the user-input │ ─ 605
│           parameters                │
└─────────────────────────────────────┘
                  ↓
┌─────────────────────────────────────┐
│  Perform connected component analysis on │
│            the error map            │ ─ 610
└─────────────────────────────────────┘
                  ↓
┌─────────────────────────────────────┐
│  Remove any row having a connected  │
│ component segment with a width less than │ ─ 615
│    the minimum acceptable error width │
└─────────────────────────────────────┘
                  ↓
┌─────────────────────────────────────┐
│ Remove any column having a connected │
│ component segment with a height less than │ ─ 620
│   the minimum acceptable error height │
└─────────────────────────────────────┘
```

FIGURE 6

FAULT DETECTION OF A PRINTED DOT-PATTERN BITMAP

BACKGROUND

A. Technical Field

The present invention pertains generally to image processing, and relates more particularly to systems and methods for fault detection of a printed dot-pattern bitmap image.

B. Background of the Invention

Printing technology is an important component of applications such as printed circuit board (hereafter, "PCB") manufacturing. In PCB manufacturing, a PCB pattern image may be printed directly onto a PCB substrate. It is important that the PCB image is accurate, because errors or aberrations in the image may result in errors in the manufactured PCB substrate.

Typically, a PCB pattern is printed as a dot-pattern image by an industrial inkjet printer. It is important to be able to calibrate such printers as well as perform quality control in order to insure that their printing performance is consistent and meets specifications. An inkjet printer head contains a set of nozzles, and the output of a particular nozzle may be correlated to regions of the dot-pattern image being printed. After periods of printer continuous use, a nozzle may become clogged or otherwise malfunction and this could lead to errors or aberrations in the image being printed.

Ceramic PCB substrates with a pattern printed by industrial inkjet printers typically are cured between successive printing cycles by a baking process. The presence of surface contaminants and the act of curing may result in the distortion of printed features. In addition to uniform shrinkage, the printed pattern is also subject to non-uniform shrinkage based on the local geometry of printed material. Distortions in the printed pattern and misfiring ink jet nozzles may also create circuit errors such as open and short circuits (topological distortions), and misalignment of circuit features (geometric distortions) between multiple printing passes.

If a nozzle's "signature" can be characterized in terms of the quality of its rendering of a region of a dot pattern, a malfunctioning printer and the cause of the malfunction could be identified through inspection of the images it produces. It would be useful to be able to identify and correct printing errors resulting from a malfunctioning printer before more costly manufacturing errors are incurred.

SUMMARY OF THE INVENTION

Embodiments of the present invention enable fault detection in a printed dot-pattern image. Certain applications of the present invention are its use in various embodiments of a system for inspection of a printed circuit board ("PCB") substrate. In embodiments, a generated distortion map is based on a comparison of a reconstructed dot-pattern image, a simulated reference bitmap, and an error map representing differences between the reconstructed dot-pattern image and the reference bitmap. In embodiments, the pixels of the distortion map are color coded to identify the locations and types of aberrations that were discovered as a result of the comparison.

In embodiments, a method for identifying aberrations within an image may comprise adjusting the image by applying a function to increase differences of intensity values of pixels within the image; generating an error map based on a comparison of a set of pixels within the image to a set of pixels within a reference bitmap of the image; removing a set of pixels from the error map based at least in part on user-input parameters; and generating a distortion map that identifies aberrations within the image. The distortion map may be generated based at least in part on the error map, the image, and the reference bitmap of the image.

In embodiments, adjusting the image may comprise calculating a distribution of intensity values of the pixels within the image; defining a lower intensity threshold value and an upper intensity threshold value; assigning a first intensity value to a pixel within the distribution if the pixel has an intensity value less than the lower intensity threshold value; assigning a second intensity value to the pixel within the distribution if the pixel has an intensity value greater than the upper intensity threshold value; and assigning a computed intensity value that is computed by applying a thresholding function to the intensity value of the pixel if the intensity value is less than the upper intensity threshold value and greater than the lower intensity threshold value.

In embodiments, generating an error map may comprise identifying a first pixel within the image and a second pixel within the reference bitmap, the pixels having corresponding locations; calculating an absolute difference between the intensity value of the first pixel and the intensity value of the second pixel; identifying a third pixel within the error map that has a location corresponding to the location of the first pixel; and assigning the absolute difference to the intensity value of the third pixel. In embodiments, assigning the absolute difference to the intensity value of the third pixel is in response to the absolute difference being greater than a threshold value.

In embodiments, removing pixels from the error map may comprise receiving a minimum acceptable error width parameter and a minimum acceptable error height parameter; generating a set of connected components within the error map by applying a connected component analysis to pixels within the error map; and removing at least one connected component from the set of connected components based on a comparison of a height and a width of a connected component to the minimum acceptable error width parameter and the minimum acceptable error height parameter.

In embodiments, removing at least one connected component from the set of connected components may comprise identifying a row of connected components within the set of connected components; removing a row of connected components if the row contains a connected component having a width that is less than the minimum acceptable error width; identifying a column of connected components within the set of connected components; and removing the column of connected components if the column contains a connected component having a height that is less than the minimum acceptable error height.

In embodiments, generating a distortion map may comprise generating an initialized distortion map that has a height and a width corresponding to the height and the width of the error map; assigning a first color intensity value to a first pixel having a location within the initialized distortion map based at least partially on an identified aberration at a corresponding pixel within the error map; and assigning a second color intensity value to a second pixel having a second location within the initialized distortion map based at least partially on an absence of an aberration at a second corresponding pixel in the error map. In embodiments, the first color intensity value may be selected from a plurality of color intensity values and relates to a particular type of aberration identified at the first corresponding pixel in the error map. In embodiments, the first color intensity value may be selected from a plurality of intensity values and identifies the aberration as being located in a foreground section of the image.

In embodiments, a method for generating a distortion map that identifies aberrations within an image may comprise generating an error map by comparing a first set of intensity values of a first set of pixels within the image to a second set of intensity values of a second set of pixels within a reference bitmap; generating an initialized distortion map that has a height and a width corresponding to the height and the width of the error map; and assigning a plurality of color intensity values to a plurality of pixels within the initialized distortion map, the color intensity value for each pixel within a subset of pixels within the plurality of pixels being based at least partially on an identified aberration of a corresponding pixel in the error map.

In embodiments, a system for generating a distortion map that identifies aberrations within an image may comprise an error map generator, coupled to receive the image and a reference bitmap, that creates an error map based on a comparison of a first set of intensity values of a first set of pixels within the image and a second set of intensity values of a second set of pixels within the reference bitmap; and a distortion map builder, coupled to receive the error map, the reference bitmap, and the image, that assigns a plurality of color intensity values to a plurality of pixels within an initialized distortion map, a color intensity value for each pixel within a subset of pixels within the plurality of pixels being based at least partially on an identified aberration of a corresponding pixels in the error map. In embodiments, creating the error map may further comprise removing pixels from a generated error map based in part on user-input parameters received by the error map generator.

Some features and advantages of the invention have been generally described in this summary section; however, additional features, advantages, and embodiments are presented herein or will be apparent to one of ordinary skill in the art in view of the drawings, specification, and claims hereof. Accordingly, it should be understood that the scope of the invention shall not be limited by the particular embodiments disclosed in this summary section.

BRIEF DESCRIPTION OF THE DRAWINGS

Reference will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

FIG. 1 illustrates examples of a simulated reference bitmap, a reconstructed bitmap image, and a distortion bitmap of a printed PCB pattern according to various embodiments of the invention.

FIG. 6 depicts a method for pruning errors on an error map according to various embodiments of the invention.

DETAILED DESCRIPTION OF THE PREFERRED EMBODIMENTS

Figure 2A:
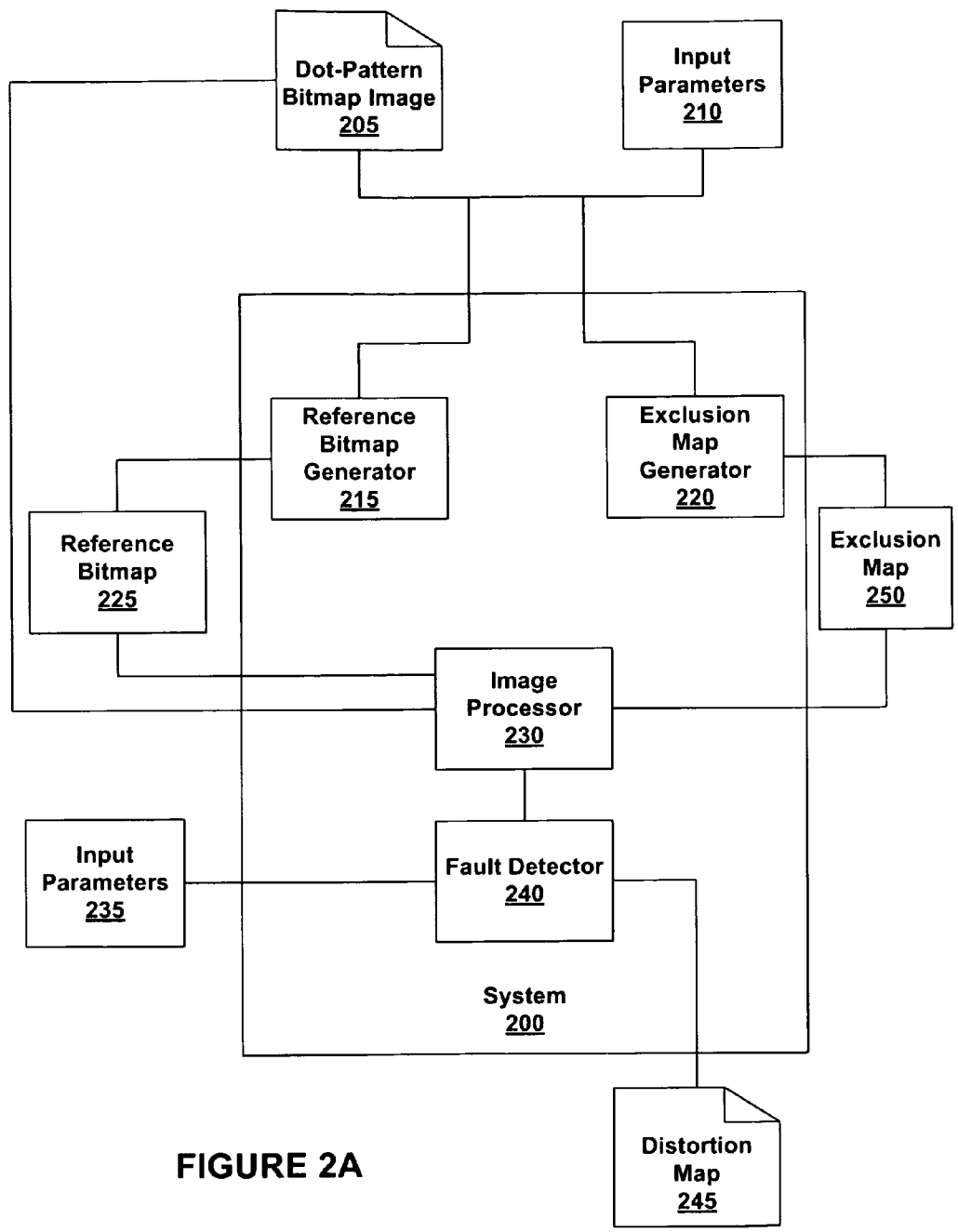
FIG. 2A depicts a block diagram of a system for inspection of a printed PCB bitmap according to various embodiments of the invention.

In the following description, for purpose of explanation, specific details are set forth in order to provide an understanding of the invention. It will be apparent, however, to one skilled in the art that the invention may be practiced without these details. One skilled in the art will recognize that embodiments of the present invention, some of which are described below, may be incorporated into a number of different systems and devices including camera, scanners, printers, computers, facsimile machine, mobile devices, including those devices with a display or camera capabilities, multimedia devices, and the like. The embodiments of the present invention may be implemented in software, hardware, firmware, or combinations thereof.

Components, or modules, shown in block diagrams are illustrative of exemplary embodiments of the invention and are meant to avoid obscuring the invention. It shall also be understood that throughout this discussion that components may be described as separate functional units, which may comprise sub-units, but those skilled in the art will recognize that the various components, or portions thereof, may be divided into separate components or may be integrated together, including integrating within a single system or component.

Furthermore, connections between components/modules within the figures are not intended to be limited to direct connections. Rather, data between these components may be modified, re-formatted, or otherwise changed by intermediary components. Also, additional or fewer connections may be used. It shall also be noted that the terms "coupled" or "communicatively coupled" shall be understood to include direct connections, indirect connections through one or more intermediary devices, and wireless connections.

Reference in the specification to "one embodiment" or "an embodiment" means that a particular feature, structure, characteristic, or function described in connection with the embodiment is included in at least one embodiment of the invention and may be in more than one embodiment. The appearances of the phrase "in one embodiment" or "in an embodiment" in various places in the specification are not necessarily all referring to the same embodiment.

Certain applications of the present invention are its use in various embodiments of a system for inspection of a printed circuit board ("PCB") substrate. A PCB pattern may be printed onto a substrate as a dot-pattern image by an industrial ink jet printer; the dot pattern is produced by an array of printer ink nozzles. After some period of continuous use of an ink jet printer, some of its nozzles may become clogged or may malfunction, and this may lead to aberrations in the dot-pattern image being printed. An aberration in a printed PCB pattern may correspond to a circuit defect such as a short or a broken connection.

An inspection system is applied to PCB images that have been printed by an ink jet printer. Such an inspection system may enable identification of faults in a printed PCB image and also may enable determination of which nozzles were associated with the locations of the identified faults on the printed image. FIG. 1 illustrates an example of fault detection in a printed PCB image according to various embodiments of the invention. A dot-pattern image of a PCB pattern 140 may be compared to a simulated reference bitmap of the PCB pattern 120, and a distortion map 160 that represents differences between the dot-pattern image 140 and the reference bitmap 120 may be generated.

FIG. 2A depicts a block diagram of a system 200 for inspection of a printed dot-pattern image according to various embodiments of the invention. System 200 receives a dot-pattern bitmap image to be inspected 205 and compares it to a simulated reference bitmap image 225 that is generated by a reference bitmap generator 215. The reference bitmap is a simulation of the dot-pattern bitmap image and is intended to exclude a majority, if not all, of the aberrations that may be caused by the printing of the image on the PCB substrate.

FIG. 1 illustrates thumbnails of an exemplary simulated reference bitmap 120 of a dot-pattern image of a PCB pattern. The simulated reference bitmap may be larger in size than the dot-pattern image on which it is based in order to increase the resolution of the reference image. In various embodiments, the size and configuration of the generated reference bitmap may be determined by user-input parameters 210 as described in U.S. patent application Ser. No. 12/031,21, entitled "Simulation of a Printed Dot-Pattern Bitmap," filed Feb. 14, 2008, which is herein incorporated by reference in its entirety.

The dot-pattern image 205 and the reference bitmap image 225 are compared by an image processor 230. A fault detector 240, configurable by user-input parameters 235, creates a distortion map 245 of aberrations that may have been discovered during the comparison of the input image 205 with the generated reference image 225. An exemplary distortion map 160 is illustrated in FIG. 1.

The input dot-pattern bitmap image 205 may be very large. Large dot-pattern bitmap images may be divided into sections and then selected sections may be compared with corresponding sections of the generated reference bitmap image. In embodiments, sections to be compared may be selected through user-input parameters 210. An "exclusion map" 250 of the dot-pattern image that is generated by an exclusion map generator 220 may be used in the selection of sections to compare. An exclusion map identifies areas of non-inspection within a dot-pattern image. In embodiments, the image processor 230 may use in part a set of sections, the input dot-pattern image 205, the reference bitmap 225, and the exclusion map 250 to generate a reconstructed dot-pattern image that may become the basis for fault detection. An exemplary reconstructed dot-pattern image 140 is illustrated in FIG. 1.

A. System Implementations

Figure 2B:
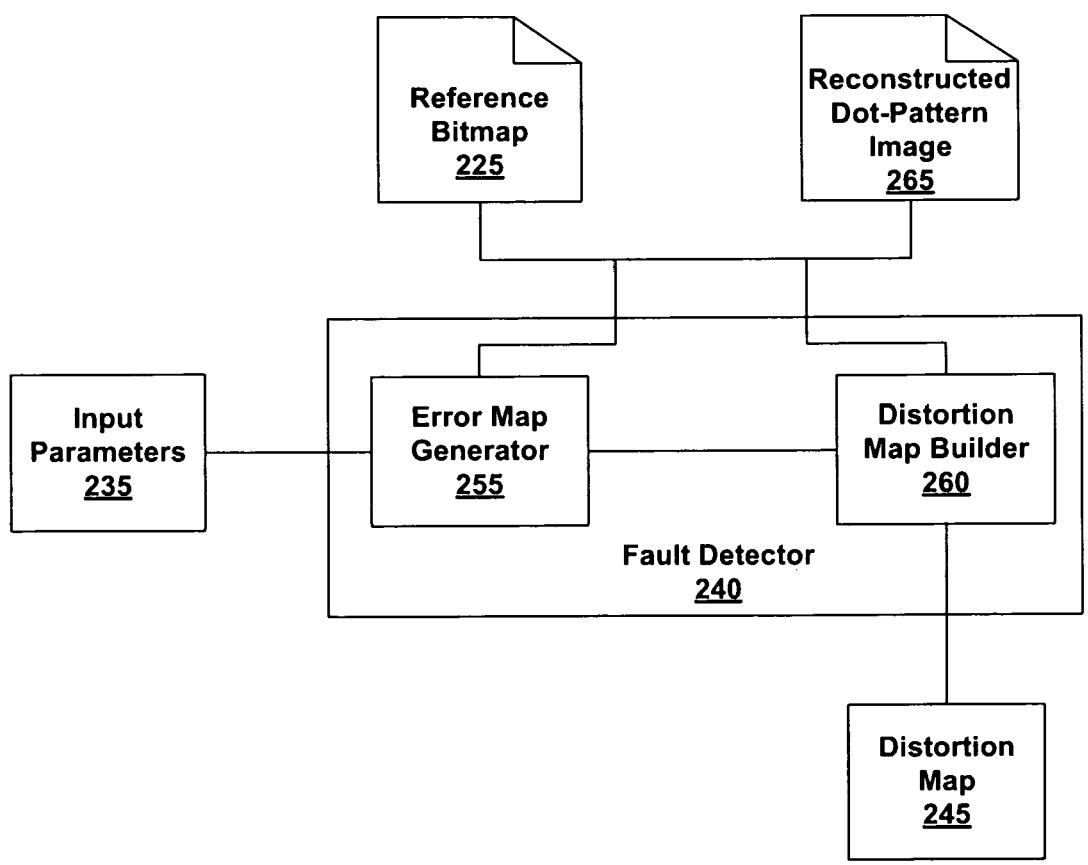
FIG. 2B depicts a block diagram of a fault detector system for generating a distortion map of faults discovered in a printed dot-pattern bitmap according to various embodiments of the invention.

FIG. 2B depicts a block diagram of a fault detector 240 according to various embodiments of the invention. Fault detector 240 receives a reference bitmap 225, a reconstructed dot-pattern image 265, and user-input parameters 235, and generates a distortion map 245 that represents the differences between the reconstructed dot-pattern image 265 and the reference bitmap 225. A fault detector 240 may be used in embodiments of inspection system 200 in order to generate a distortion map 245 that identifies faults within a dot-pattern bitmap image 205.

In embodiments of inspection system 200, an image of a printed dot pattern that cannot be captured in a single scan is reconstructed from a set of snapshots of sections of the printed dot pattern. The reconstructed dot-pattern image 265 is inspected for errors by comparing it to the reference bitmap 225.

In embodiments, error map generator 255 produces an "error map" image that is the result of comparing the intensity values of pixels within a reconstructed dot-pattern image 265 with the intensity values of corresponding pixels within a simulated reference bitmap of the dot-pattern image 225. The error map is a representation of aberrations in the reconstructed dot-pattern image.

In embodiments, a reconstructed dot-pattern image 265 may be enhanced by applying noise-clipping and contrast stretching to the intensity values of the pixels within the image. For example, a lower intensity threshold a and an upper intensity threshold b may be selected. Noise clipping of pixel intensity values within an image may be performed by assigning an intensity value of 0 (black) to pixels having an intensity value less than a and assigning an intensity value of 255 (white) to pixels having an intensity value greater than b. The characteristics of the intensity distribution of the image pixels may be used to select lower intensity threshold value a and upper intensity threshold value b, but those skilled in the art will recognize that a variety of factors may determine the choice of specific values to use for intensity threshold values a and b, and that this choice is not critical to the invention.

Contrast stretching may be applied to the set of pixel intensity values that are greater than the lower intensity threshold value a and less than the upper intensity value b. Contrast stretching enhances differences within the set of intensity values by using a thresholding function h to compute a new intensity value h(I) for each intensity value I in the set of intensity values. Those skilled in the art will recognize that a variety of thresholding functions exist and that the choice of a thresholding function is not critical to the invention.

In embodiments, an error map with the same configuration as the reconstructed dot-pattern image is generated by computing each error map pixel's intensity value $I_{err}$ based on a function comparing intensity values of corresponding pixels in an enhanced reconstructed image h(I) and the reference bitmap $I_{ref}$. For example, $I_{err}$ may be computed using the function:

$$I_{err} = |h(I) - I_{ref}| > T$$

where T is a threshold value to enhance the contrast in the error map.

In embodiments, a generated error map may be updated to represent only significant aberrations. A significant aberration may be determined by user-input parameters 235 that define a minimum acceptable error width and height. These parameters may be represented in numbers of pixels. In embodiments, a connected component analysis may be performed on an error map, and then the error map may be updated by removing connected component segments that have a width and height below the minimum acceptable error width and height.

In embodiments, distortion map builder 260 produces a distortion map 245 that is an error map which has been color-coded to highlight locations and types of identified aberrations. An exemplary distortion map 160 is illustrated in FIG. 1.

In embodiments, distortion map builder 260 assigns colors to the pixels in the distortion map based on the intensity values and locations of corresponding pixels on the reconstructed dot-pattern image 265, the reference bitmap 225, and a generated error map. One skilled in the art will recognize that various types of maps with difference characteristics may be used to illustrate distortions on the reconstructed dot pattern image 265.

B. Methods for Generating a Distortion Map Representing Image Faults

As was previously discussed, faults within a dot-pattern bitmap image may be represented as a distortion map that identifies the differences between a reconstructed dot-pattern image and a reference bitmap of the dot-pattern image. In embodiments, an image of a printed dot pattern that cannot be captured in a single scan is reconstructed from a set of snapshots of sections of the printed dot pattern. The reconstructed dot-pattern image is inspected for errors by comparing it to the reference bitmap, and the result of the inspection is a distortion map.

Figure 3:
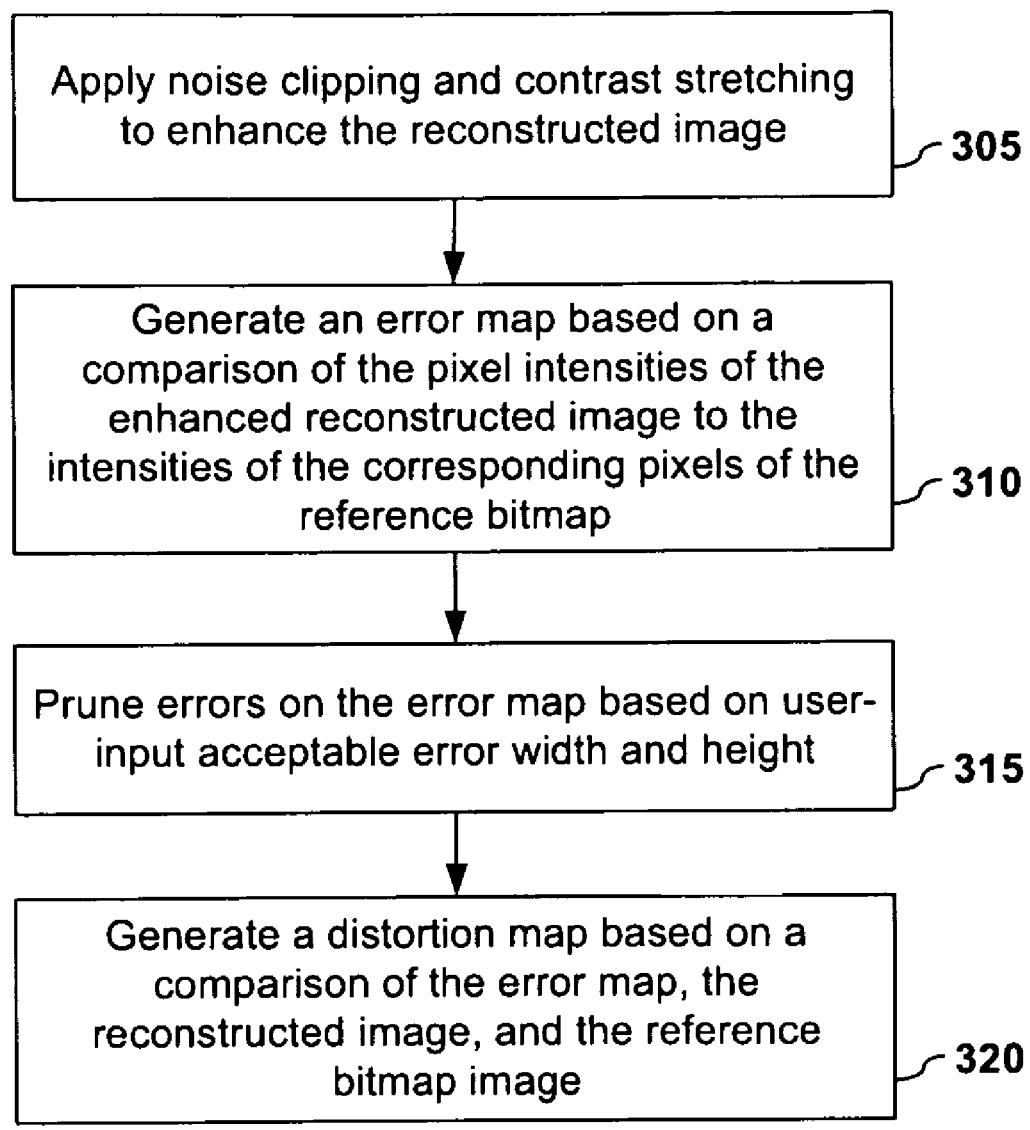
FIG. 3 depicts a method for generating a distortion map of faults discovered in a printed dot-pattern bitmap according to various embodiments of the invention.

FIG. 3 depicts a method 300, independent of structure, for generating a distortion map of faults discovered in a printed dot-pattern bitmap according to various embodiments of the invention. Method 300 may be implemented in embodiments of fault detector 240 in system 200. Method 300 comprises the steps of enhancing the reconstructed dot-pattern image 305; generating an error map 310; updating the generated error map 315; and generating a distortion map based on the generated error map, the reconstructed dot-pattern image, and the reference bitmap 320. Method 300 may be implemented in embodiments of fault detector 240 in system 200.

1. Generating an Error Map

In embodiments, an "error map" image is the result of comparing the intensity values of pixels within a reconstructed dot-pattern image with the intensity values of corresponding pixels within a simulated reference bitmap of the dot-pattern image. The error map is a representation of aberrations in the reconstructed dot-pattern image.

a) Noise Clipping and Contrast Stretching of Pixel Intensity Values

In embodiments, a reconstructed dot-pattern image may be enhanced by applying noise-clipping and contrast stretching to the intensity values of the pixels within the image 305.

Figure 4:
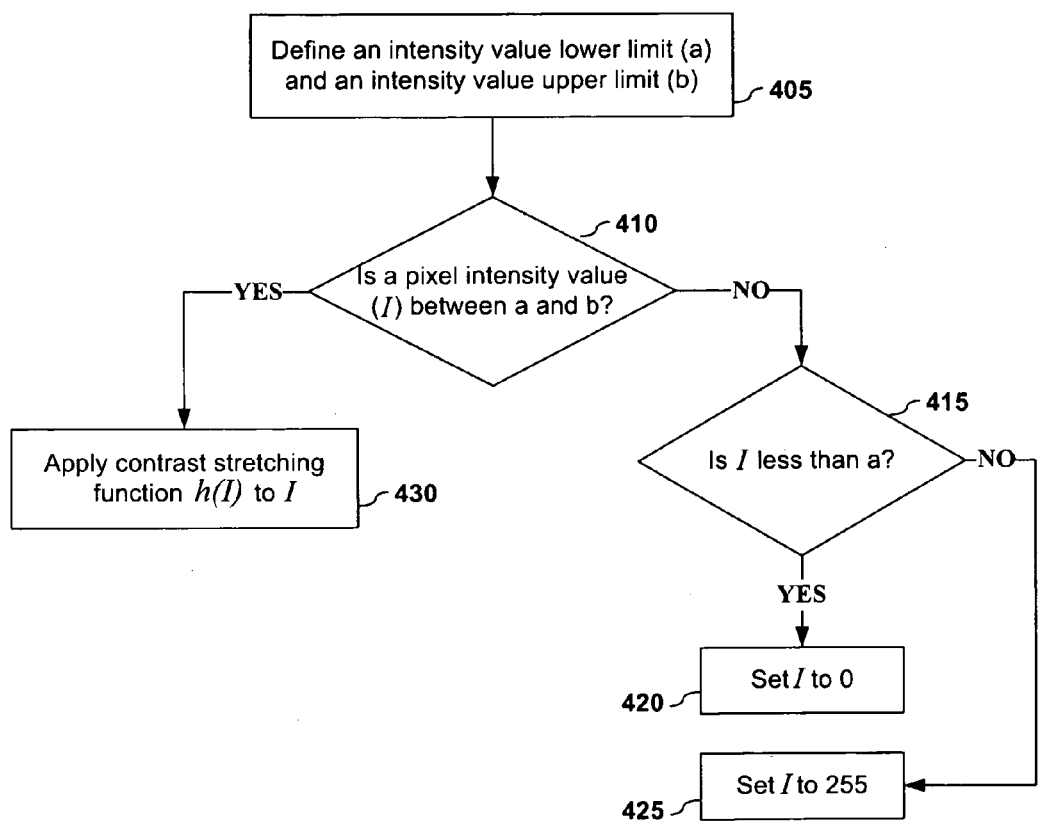
FIG. 4 depicts a method for generating an error map based on a comparison of pixel intensities in a printed dot-pattern bitmap and a simulated reference bitmap according to various embodiments of the invention.

FIG. 4 depicts a method 400, independent of structure, for applying noise clipping to intensity values of pixels within an image according to various embodiments of the invention. Method 400 may be implemented within step 305 of embodiments of method 300, and in embodiments of error map generator 255.

In embodiments, a lower intensity threshold a and an upper intensity threshold b may be selected 405. Noise clipping of pixel intensity values within an image may be performed by assigning an intensity value of 0 (black) 420 to pixels having an intensity value less than a 415 and assigning an intensity value of 255 (white) 425 to pixels having an intensity value greater than b 415. The characteristics of the intensity distribution of the image pixels may be used to select lower intensity threshold value a and upper intensity threshold value b, but those skilled in the art will recognize that a variety of factors may determine the choice of specific values to use for intensity threshold values a and b, and that this choice is not critical to the invention.

Figure 5A:
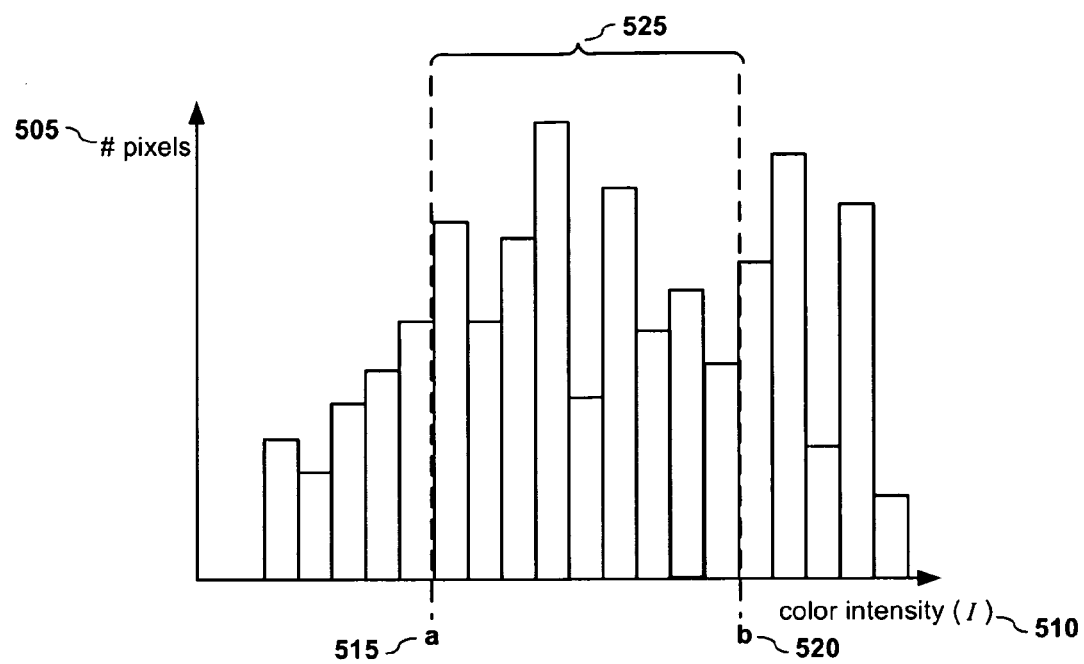
FIG. 5A illustrates the application of noise clipping to the intensity values of a distribution of pixels within a dot-pattern image according to various embodiments of the invention.

FIG. 5A depicts an exemplary histogram representation of a distribution of intensity values 510 of pixels within an image 505 according to various embodiments of the invention. The lower intensity threshold value a 515 and the upper intensity threshold value b 520 are designated by vertical dotted lines overlaid onto the histogram.

In embodiments, contrast stretching may be applied to the set of pixel intensity values within a distribution that are greater than the lower intensity threshold value a and less than the upper intensity value b (the bracketed region of intensity values 525 on the histogram depicted in FIG. 5A). Contrast stretching enhances differences within the set of intensity values by using a thresholding function h to compute a new intensity value h(I) for each intensity value I in the set of intensity values. Those skilled in the art will recognize that a variety of thresholding functions exist and that the choice of a thresholding function is not critical to the invention.

Figure 5B:
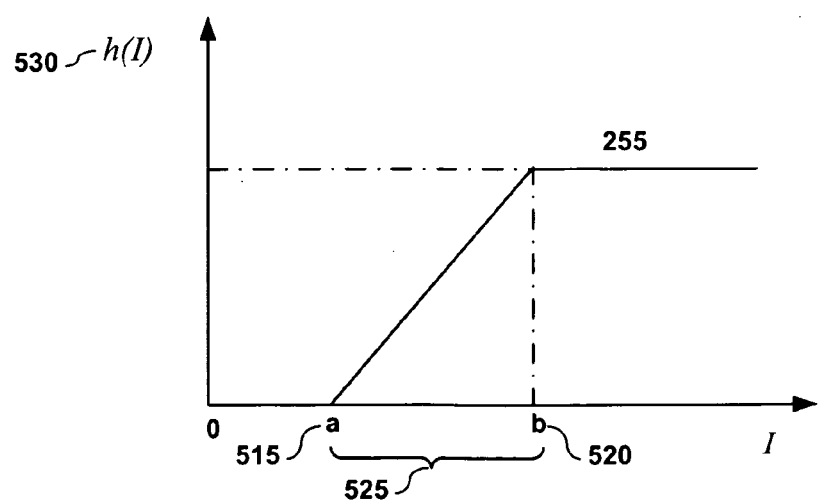
FIG. 5B illustrates the application of contrast stretching to the intensity values of a distribution of pixels within a dot-pattern image according to various embodiments of the invention.

FIG. 5B depicts a graphical representation of an exemplary thresholding function h that includes both noise clippling and contrast stretching according to various embodiments of the invention. This exemplary function h is applied to the exemplary distribution of pixel intensity values depicted in FIG. 5A, and may be implemented as step 305 of embodiments of method 300. The value of h(I) 530 is 0 for pixels having an intensity value I that is less than the lower intensity threshold value a 515, and value of h(I) 530 is 255 for pixels having an intensity value I that is greater than the upper intensity threshold value b 520. In the example, h(I) 530 becomes a linear function for values of I within the distribution that are greater than the lower intensity threshold value a 515 and less than the upper intensity value b 520 (the bracketed region of intensity values I 525).

b) Generating and Updating an Error Map

In embodiments, an error map with the same configuration as the reconstructed dot-pattern image is generated by computing each error map pixel's intensity value $I_{err}$ based on a function comparing intensity values of corresponding pixels in an enhanced reconstructed image h(I) and the reference bitmap $I_{ref}$ 310.

For example, in embodiments $I_{err}$ may be computed using the function:

$$I_{err}=|h(I)-I_{ref}|>T$$

where T is a threshold value to enhance the contrast in the error map.

FIG. 6 depicts a method 600, independent of structure, for pruning errors on an error map according to various embodiments of the invention. Method 600 may be implemented as step 315 in embodiments of method 300 and in embodiments of error map generator 255.

In embodiments, a generated error map may be updated to represent only significant aberrations by pruning aberrations that do not meet specified criteria. A significant aberration may be determined by user-input parameters that define a minimum acceptable error width and height 605. These parameters may be represented in numbers of pixels.

The error map may be segmented into layers, and a connected component analysis ("CCA") may be performed on the foreground pixels of the error map 610. One example of a CCA is to scan each row of pixels within an image, determining the component label of each pixel in a row. To determine the component label of a pixel, the principle of "8-connectivity" is applied so that the pixel's label is based on the labels of the 8 pixels within a 3-by-3 neighborhood surrounding the pixel. One skilled in the art will recognize that this is an example, and that various methods of CCA may be used on images. A connected component may be defined as a bounded region enclosing a connected set of foreground pixels.

The minimum acceptable error width and height may be used to prune the set of connected component segments that have been identified within the error map. The rows of connected components may be scanned, and any row having a connected component segment with a width less than the minimum acceptable error width may be removed 615. The columns of connected components may be scanned, and any column having a connected component segment with a height less than the minimum acceptable error height may be removed 620.

2. Generating a Distortion Map

In embodiments, a distortion map is an error map which has been color-coded to highlight locations and types of identified aberrations. An exemplary distortion map 160 is illustrated in FIG. 1.

Figure 7:
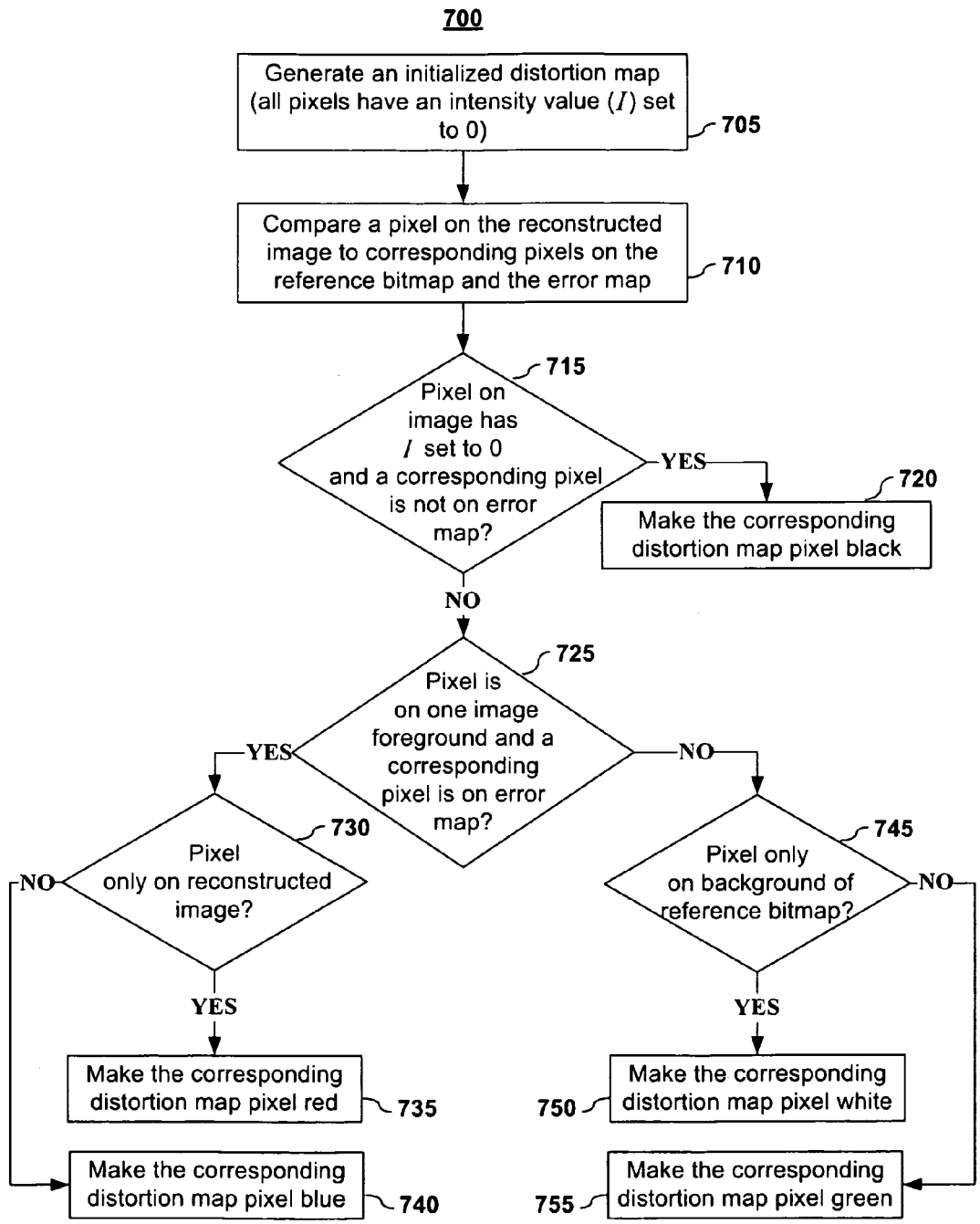
FIG. 7 depicts a method for generating a distortion map according to various embodiments of the invention.

FIG. 7 depicts a method 700, independent of structure, for generating a distortion map based on a comparison of a reconstructed dot-pattern image, a simulated reference bitmap, and an error map representing differences between the reconstructed dot-pattern image and the reference bitmap. Method 700 may be implemented as step 320 in embodiments of method 300, and in embodiments of distortion map builder 260.

In embodiments, an initialized distortion map having the same height and width as the error map is generated. The intensity value $I_{distortion}$ of all of the pixels is set to 0 (black) 705. The intensity value $I_{distortion}$ of each pixel then is re-assigned based on the result of a comparison of corresponding pixels on the reconstructed dot-pattern image, the simulated reference bitmap, and the error map 710.

The intensity value $I_{distortion}$ of a pixel on the distortion map remains set to 0 720 if there is a corresponding pixel on the reconstructed dot-pattern image that has an intensity value I of 0 and there is no corresponding pixel on the error map 715.

If there is a corresponding pixel on the error map 715, the intensity value $I_{distortion}$ of the pixel on the distortion map will be assigned a color intensity value. If the pixel is in the foreground of an image, the aberration indicated by the error map involves a PCB component and thus may represent a fault 725. If there is a corresponding pixel on only the reconstructed image foreground 730, $I_{distortion}$ will be set to red 735. If there is a corresponding pixel on only the reference bitmap foreground 730, $I_{distortion}$ will be set to blue 740.

If the pixel is in the background of an image, the aberration indicated by the error map does not involve a PCB component and thus may not represent a fault 725. If there is a corresponding pixel on only the reference bitmap background 745, $I_{distortion}$ will be set to white 750. If there is a corresponding pixel on only the reconstructed image background 745, $I_{distortion}$ will be set to green 755.

C. Computing System Implementations

It shall be noted that the present invention may be implemented in any instruction-execution/computing device or system capable of processing the data, including without limitation, a general-purpose computer and a specific computer, such as one intended for data processing. The present invention may also be implemented into other computing devices and systems, including without limitation, a digital camera, a printer, a scanner, a multiple function printer/scanner, a facsimile machine, a multimedia device, and any other device that processes, captures, transmits, or stores data. Furthermore, within any of the devices, aspects of the present invention may be implemented in a wide variety of ways including software, hardware, firmware, or combinations thereof. For example, the functions to practice various aspects of the present invention may be performed by components that are implemented in a wide variety of ways including discrete logic components, one or more application specific integrated circuits (ASICs), and/or program-controlled processors. It shall be noted that the manner in which these items are implemented is not critical to the present invention.

Figure 8:
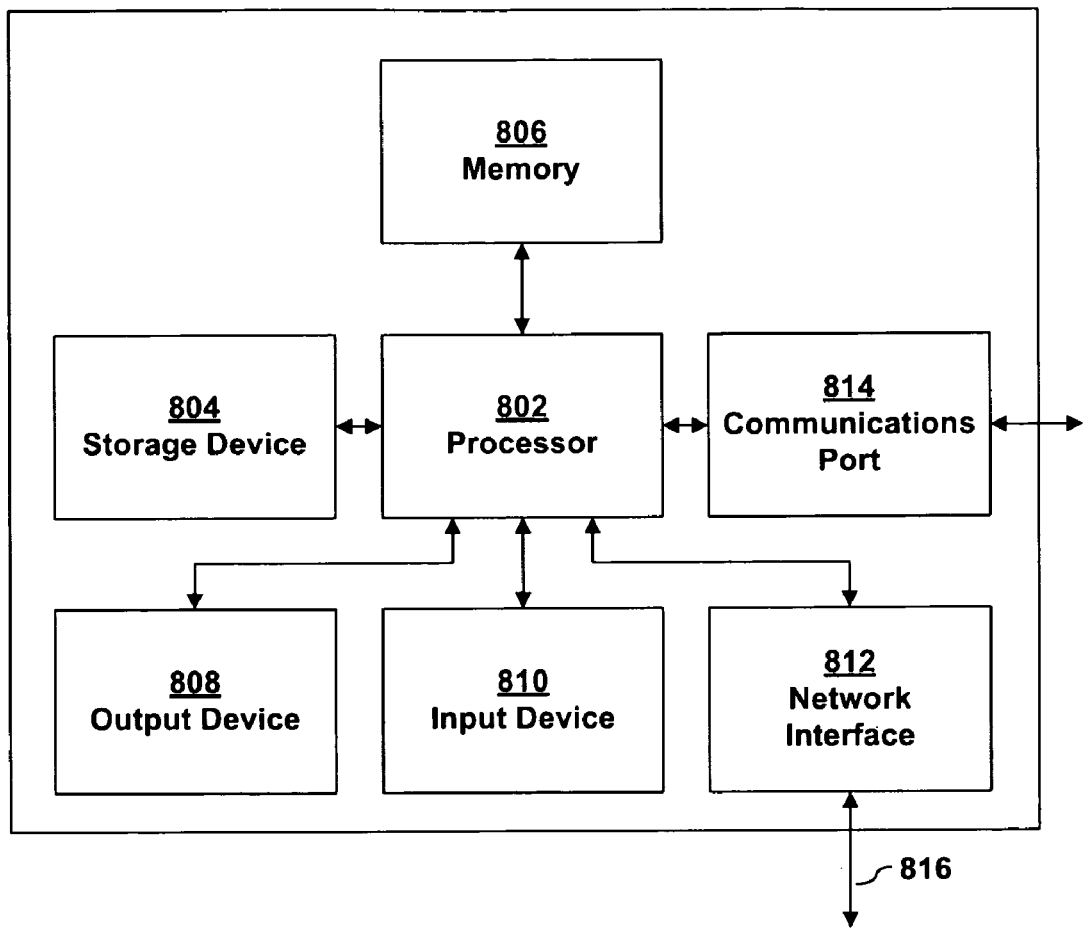
FIG. 8 depicts a block diagram of a computing system.

FIG. 8 depicts a functional block diagram of an embodiment of an instruction-execution/computing device 800 that may implement or embody embodiments of the present invention. As illustrated in FIG. 8, a processor 802 executes software instructions and interacts with other system components. In an embodiment, processor 802 may be a general purpose processor such as an AMD processor, an INTEL processor, a SUN MICROSYSTEMS SPARC, or a POWERPC compatible-CPU, or the processor may be an application specific processor or processors. A storage device 804, coupled to processor 802, provides long-term storage of data and software programs. Storage device 804 may be a hard disk drive and/or another device capable of storing data, such as a computer-readable media (e.g., diskettes, tapes, compact disk, DVD, and the like) drive or a solid-state memory device. Storage device 804 may hold programs, instructions, and/or data for use with processor 802. In an embodiment, programs or instructions stored on or loaded from storage device 804 may be loaded into memory 806 and executed by processor 802. In an embodiment, storage device 804 holds programs or instructions for implementing an operating system on processor 802. In one embodiment, possible operating systems include, but are not limited to, UNIX, AIX, LINUX, Microsoft Windows, and the Apple MAC OS. In embodiments, the operating system executes on, and controls the operation of, the computing system 800.

An addressable memory 806, coupled to processor 802, may be used to store data and software instructions to be executed by processor 802. Memory 806 may be, for example, firmware, read only memory (ROM), flash memory, non-volatile random access memory (NVRAM), random access memory (RAM), or any combination thereof. In one embodiment, memory 806 stores a number of software objects, otherwise known as services, utilities, components, or modules. One skilled in the art will also recognize that storage 804 and memory 806 may be the same items and function in both capacities. In an embodiment, one or more of the components of FIGS. 2A and 2B may be modules stored in memory 804, 806 and executed by processor 802.

In an embodiment, computing system 800 provides the ability to communicate with other devices, other networks, or both. Computing system 800 may include one or more network interfaces or adapters 812, 814 to communicatively couple computing system 800 to other networks and devices. For example, computing system 800 may include a network interface 812, a communications port 814, or both, each of which are communicatively coupled to processor 802, and which may be used to couple computing system 800 to other computer systems, networks, and devices.

In an embodiment, computing system 800 may include one or more output devices 808, coupled to processor 802, to facilitate displaying graphics and text. Output devices 808 may include, but are not limited to, a display, LCD screen, CRT monitor, printer, touch screen, or other device for displaying information. Computing system 800 may also include a graphics adapter (not shown) to assist in displaying information or images on output device 808.

One or more input devices 810, coupled to processor 802, may be used to facilitate user input. Input device 810 may include, but are not limited to, a pointing device, such as a mouse, trackball, or touchpad, and may also include a keyboard or keypad to input data or instructions into computing system 800.

In an embodiment, computing system 800 may receive input, whether through communications port 814, network interface 812, stored data in memory 804/806, or through an input device 810, from a scanner, copier, facsimile machine, or other computing device.

One skilled in the art will recognize no computing system is critical to the practice of the present invention. One skilled in the art will also recognize that a number of the elements described above may be physically and/or functionally separated into sub-modules or combined together.

It shall be noted that embodiments of the present invention may further relate to computer products with a computer-readable medium that have computer code thereon for performing various computer-implemented operations. The media and computer code may be those specially designed and constructed for the purposes of the present invention, or they may be of the kind known or available to those having skill in the relevant arts. Examples of computer-readable media include, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices. Examples of computer code include machine code, such as produced by a compiler, and files containing higher level code that are executed by a computer using an interpreter.

While the invention is susceptible to various modifications and alternative forms, specific examples thereof have been shown in the drawings and are herein described in detail. It should be understood, however, that the invention is not to be limited to the particular forms disclosed, but to the contrary, the invention is to cover all modifications, equivalents, and alternatives falling within the scope of the appended claims.

What is claimed is:

1. A method for identifying aberrations within an image comprising pixels, the method comprising:
    adjusting the image by applying a function to increase differences of intensity values of a plurality of pixels within the image;
    generating an error map based on a comparison of a first set of pixels within the image to a second set of pixels within a reference bitmap of the image;
    removing a third set of pixels from the error map based at least in part on user-input parameters; and
    generating a distortion map that identifies aberrations within the image, the distortion map being generated based at least in part on the error map, the image, and the reference bitmap of the image.

2. The method of claim 1 wherein the step of adjusting the image comprises:
    calculating a distribution of intensity values of the pixels within the image;
    defining a lower intensity threshold value and an upper intensity threshold value;
    responsive to a pixel within the distribution having an intensity value less than the lower intensity threshold value, assigning a first intensity value to the pixel;
    responsive to the pixel within the distribution having an intensity value that is greater than the upper intensity threshold value, assigning a second intensity value to the pixel; and
    responsive to the pixel within the distribution having an intensity value greater than the lower intensity threshold value and less than the upper intensity value, assigning a computed intensity value to the pixel, the computed intensity value being generated by applying a threshold function to the intensity value.

3. The method of claim 1 wherein the step of generating an error map comprises:
    identifying a first pixel within the image and a second pixel within the reference bitmap, wherein the first pixel and the second pixel have corresponding locations;
    calculating an absolute difference between a first intensity value of the first pixel and a second intensity value of the second pixel;
    identifying a third pixel within the error map, wherein the third pixel and the first pixel have corresponding locations; and
    assigning the absolute difference to a third intensity value of the third pixel.

4. The method of claim 3 wherein assigning the absolute difference to the third intensity value is in response to the absolute difference being greater than a threshold value.

5. The method of claim 1 wherein the step of removing pixels from the error map comprises:
    receiving a minimum acceptable error width parameter and a minimum acceptable error height parameter;
    generating a set of connected components within the error map by applying a connected component analysis to pixels within the error map, wherein a connected component comprises at least two adjacent pixels; and
    removing at least one connected component from the set of connected components based on a comparison of a height and a width of the at least one connected component to the minimum acceptable error width parameter and the minimum acceptable error height parameter.

6. The method of claim 5 wherein the step of removing the at least one connected component from the set of connected components comprises:
    identifying a row of connected components within the set of connected components;
    responsive to the row of connected components containing a connected component having a width that is less than the minimum acceptable error width, removing the row of connected components;
    identifying a column of connected components within the set of connected components; and
    responsive to the column of connected components containing a connected component having a height that is less than the minimum acceptable error height, removing the column of connected components.

7. The method of claim 1 wherein the step of generating a distortion map comprises:
    generating an initialized distortion map comprising pixels, the initialized distortion map having a height and a width corresponding to the height and the width of the error map;
    assigning a first color intensity value to a first pixel having a first location within the initialized distortion map, the first color intensity value being based at least partially on an identified aberration at a first corresponding pixel in the error map; and
    assigning a second color intensity value to a second pixel having a second location within the initialized distortion map, the second color intensity value being based at least partially on an absence of an aberration at a second corresponding pixel in the error map.

8. The method of claim 7 wherein the first color intensity value is selected from a plurality of color intensity values and relates to a particular type of aberration identified at the first corresponding pixel in the error map.

9. The method of claim 7 wherein the first color intensity value is selected from a plurality of intensity values and identifies the aberration as being located in a foreground section of the image.

10. A non-transitory computer readable medium having instructions for performing the method of claim 1.

11. A system for generating a distortion map that identifies aberrations within an image, the system comprising:
   an error map generator coupled to receive the image and a reference bitmap, the error map generator creates an error map based on a comparison of a first set of intensity values of a first set of pixels within the image and a second set of intensity values of a second set of pixels within the reference bitmap; and
   a distortion map builder, coupled to receive the error map, the reference bitmap, and the image, the distortion map builder assigns a plurality of color intensity values to a plurality of pixels within an initialized distortion map, a color intensity value for each pixel within a subset of pixels within the plurality of pixels being based at least partially on an identified aberration of a corresponding pixel in the error map.

12. The system of claim 11 wherein creating the error map further comprises removing pixels from a generated error map based in part on user-input parameters received by the error map generator.

13. The system of claim 11 wherein assigning the plurality of color intensity values to the plurality of pixels within the initialized distortion map is performed by a method comprising the steps of:
   assigning a first color intensity value to a first pixel having a first location within the initialized distortion map, the first color intensity value being based at least partially on an identified aberration at a first corresponding pixel in the error map; and
   assigning a second color intensity value to a second pixel having a second location within the initialized distortion map, the second color intensity value being based at least partially on an absence of an aberration at a second corresponding pixel in the error map.

14. The system of claim 13 wherein the first color intensity value is selected from a plurality of color intensity values and relates to a particular type of aberration identified at the first corresponding pixel in the error map.

\* \* \* \* \*